(12) United States Patent
Martin et al.

(10) Patent No.: US 8,206,154 B2
(45) Date of Patent: Jun. 26, 2012

(54) DENTITION SCORE

(75) Inventors: John A. Martin, State College, PA (US); Carl F. Loeb, Mount Vernon, WA (US)

(73) Assignee: PreViser Corporation, Mount Vernon, WA (US)

( * ) Notice: Subject to any disclaimer, the term of this patent is extended or adjusted under 35 U.S.C. 154(b) by 575 days.

(21) Appl. No.: 12/173,510

(22) Filed: Jul. 15, 2008

(65) Prior Publication Data

US 2010/0015575 A1  Jan. 21, 2010

(51) Int. Cl.
*A61C 5/00* (2006.01)
(52) U.S. Cl. ............................................. 433/215
(58) Field of Classification Search .............. 433/215, 433/229; 705/2–3
See application file for complete search history.

(56) References Cited

U.S. PATENT DOCUMENTS

2007/0184411 A1* 8/2007 Stapleton .................. 433/215

OTHER PUBLICATIONS

Evaluation of an oral health scoring system by dentists in general dental practice. F.J.T. Burke, M. Busby, S. McHugh, S. Delargy, A. Mullins, R. Matthews. British Dental Journal vol. 194, No. 4 Feb. 22, 2003 pp. 215-218.*
Armitage, Gary C., "Development of a Classification System for periodontal Diseases and Conditions", Annals of Periodontology, 4:1-6, Dec. 1999.
Edwards, W., "Appendix A. 4 Tools for Identifying & Evaluating Option", "Multiattribute Evaluation", www.ctg.albany.edu, 6 pages, 2003.
Singer, Lawrence J., "Dental Wellness Index Helps Practices Predictably measure Treatment Outcomes and Assure That Quality Levels Remain High", PennWell, Dental Economics, DWI—Aug. 1998, www.dentaleconomics.com/articles/print/html?id=116189&bPool=DE.pennet.com, Jun. 24, 2008, pp. 1-5.

* cited by examiner

*Primary Examiner* — Heidi M Eide
(74) *Attorney, Agent, or Firm* — Fish & Richardson P.C.

(57) ABSTRACT

Methods, systems, algorithms, and uses for dentition scores having clinical applicability for an individual patient are described herein. The scores increase as a condition worsens and decrease with treatment. The score can be used to communicate the status of a patient's dentitions to the patient, to an insurer, or to another health care professional.

21 Claims, 10 Drawing Sheets

| Percentage of teeth with caries | 120 |
| Percentage of teeth with a restoration | 122 |
| Value for carious teeth | 124 |
| Value for restored teeth | 126 |
| Number of teeth that should be replaced | 128 |
| Percentage of optimal teeth that should be replaced | 130 |
| Value for tooth replacement | 132 |
| Value for missing teeth that need to be replaced | 134 |

| How many teeth are optimal for the patient, *excluding third molars*? | 100 |
| How many natural teeth are visible, *excluding third molars*? | 102 |
| How many teeth have any type of restoration, including crowns and veneers? | 104 |
| How many teeth have caries or defective restoration? | 106 |
| For the teeth that have been replaced how many are not removable (fixed, permanent) by the patient? | 108 |
| For the teeth that have been replaced how many are removable by the patient? | 110 |

FIG. 2

| Percentage of teeth with caries | 120 |
| Percentage of teeth with a restoration | 122 |
| Value for carious teeth | 124 |
| Value for restored teeth | 126 |
| Number of teeth that should be replaced | 128 |
| Percentage of optimal teeth that should be replaced | 130 |
| Value for tooth replacement | 132 |
| Value for missing teeth that need to be replaced | 134 |

FIG. 3

Primary Teeth

| Upper Teeth | Erupt | Shed |
|---|---|---|
| Central Incisor | 8-12 Months | 6-7 Years |
| Lateral Incisor | 9-13 Months | 7-8 Years |
| Canine (Cuspid) | 16-22 Months | 10-12 Years |
| First Molar | 13-19 Months | 9-11 Years |
| Second Molar | 25-33 Months | 10-12 Years |

| Lower Teeth | Erupt | Shed |
|---|---|---|
| Second Molar | 23-31 Months | 10-12 Years |
| First Molar | 14-18 Months | 9-11 Years |
| Canine (Cuspid) | 17-23 Months | 9-12 Years |
| Lateral Incisor | 10-16 Months | 7-8 Years |
| Central Incisor | 6-10 Months | 6-7 Years |

FIG. 4

Permanent Tooth Eruption Chart

| Upper Teeth | Erupt |
|---|---|
| Central Incisor | 7-8 yrs. |
| Lateral Incisor | 8-9 yrs. |
| Canine (cuspid) | 11-12 yrs. |
| First premolar (first bicuspid) | 10-11 yrs. |
| Second premolar (second bicuspid) | 10-12 yrs. |
| First molar | 6-7 yrs. |
| Second molar | 12-13 yrs. |
| Third molar (wisdom tooth) | 17-21 yrs. |

| Lower Teeth | Erupt |
|---|---|
| Third molar (wisdom tooth) | 17-21 yrs. |
| Second molar | 11-13 yrs. |
| First molar | 6-7 yrs. |
| Second premolar (second bicuspid) | 11-12 yrs. |
| First premolar (first bicuspid) | 10-12 yrs. |
| Canine (cuspid) | 9-10 yrs. |
| Lateral Incisor | 7-8 yrs. |
| Central Incisor | 6-7 yrs. |

FIG. 5

| Column | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Patient | Example | Optimal teeth | Visible teeth | Restored | Caries | Fixed | Removable | Percentage of teeth with caries | Percentage of teeth with a restoration | Value for carious teeth | Value for restored teeth | Number of teeth that should be replaced | Percentage of optimal teeth that should be replaced | Value for tooth replacement | Value for missing teeth that need to be replaced | Caries Score | Prosthetic Score |
| A | 1 | 28 | 27 | 5 | 2 | 1 | 0 | 7 | 18 | 1 | 3 | 1 | 4 | 1 | 0 | 13 | 2 |
| A | 2 | 28 | 26 | 4 | 0 | 1 | 0 | 0 | 15 | 0 | 3 | 2 | 8 | 1 | 0 | 3 | 10 |
| A | 3 | 27 | 26 | 4 | 0 | 1 | 0 | 0 | 15 | 0 | 3 | 1 | 4 | 1 | 0 | 3 | 2 |
| B | 4 | 24 | 24 | 8 | 0 | 0 | 0 | 0 | 33 | 0 | 4 | 0 | 0 | 0 | 0 | 4 | 1 |
| B | 5 | 24 | 24 | 8 | 3 | 0 | 0 | 12 | 33 | 2 | 4 | 0 | 0 | 0 | 0 | 24 | 1 |
| B | 6 | 24 | 24 | 10 | 0 | 0 | 0 | 0 | 41 | 0 | 5 | 0 | 0 | 0 | 0 | 5 | 1 |
| C | 7 | 28 | 26 | 4 | 0 | 2 | 0 | 0 | 15 | 0 | 3 | 2 | 8 | 1 | 0 | 3 | 2 |
| C | 8 | 28 | 26 | 0 | 0 | 2 | 0 | 0 | 0 | 0 | 1 | 2 | 8 | 1 | 0 | 1 | 2 |
| D | 9 | 28 | 28 | 22 | 6 | 0 | 0 | 21 | 78 | 2 | 9 | 0 | 0 | 0 | 0 | 29 | 1 |
| D | 10 | 28 | 22 | 16 | 0 | 0 | 0 | 0 | 72 | 0 | 8 | 6 | 22 | 3 | 5 | 8 | 39 |
| D | 11 | 28 | 22 | 16 | 2 | 0 | 6 | 8 | 72 | 1 | 8 | 6 | 22 | 3 | 0 | 8 | 3 |
| E | 12 |  | 24 | 6 | 0 |  |  | 0 | 25 | 0 | 4 | N/A | N/A | N/A | N/A | 14 | N/A |
| E | 13 |  | 24 | 8 | 2 |  |  | 0 | 33 | 0 | 4 | N/A | N/A | N/A | N/A | 4 | N/A |
| E | 14 |  | 28 | 2 | 0 |  |  | 0 | 7 | 0 | 2 | N/A | N/A | N/A | N/A | 2 | N/A |

FIG. 6

| Caries | | Caries | | Caries | | Caries | |
|---|---|---|---|---|---|---|---|
| Percentage of teeth with caries | Value | Percentage of teeth with caries | Value | Percentage of teeth with caries | Value | Percentage of teeth with caries | Value |
| 100% | 9 | 75% | 7 | 50% | 5 | 25% | 3 |
| 99% | 9 | 74% | 7 | 49% | 5 | 24% | 3 |
| 98% | 9 | 73% | 7 | 48% | 5 | 23% | 3 |
| 97% | 9 | 72% | 7 | 47% | 5 | 22% | 2 |
| 96% | 9 | 71% | 7 | 46% | 5 | 21% | 2 |
| 95% | 9 | 70% | 7 | 45% | 5 | 20% | 2 |
| 94% | 9 | 69% | 7 | 44% | 5 | 19% | 2 |
| 93% | 9 | 68% | 7 | 43% | 4 | 18% | 2 |
| 92% | 9 | 67% | 7 | 42% | 4 | 17% | 2 |
| 91% | 9 | 66% | 7 | 41% | 4 | 16% | 2 |
| 90% | 9 | 65% | 6 | 40% | 4 | 15% | 2 |
| 89% | 9 | 64% | 6 | 39% | 4 | 14% | 2 |
| 88% | 9 | 63% | 6 | 38% | 4 | 13% | 2 |
| 87% | 9 | 62% | 6 | 37% | 4 | 12% | 2 |
| 86% | 8 | 61% | 6 | 36% | 4 | 11% | 1 |
| 85% | 8 | 60% | 6 | 35% | 4 | 10% | 1 |
| 84% | 8 | 59% | 6 | 34% | 4 | 9% | 1 |
| 83% | 8 | 58% | 6 | 33% | 3 | 8% | 1 |
| 82% | 8 | 57% | 6 | 32% | 3 | 7% | 1 |
| 81% | 8 | 56% | 6 | 31% | 3 | 6% | 1 |
| 80% | 8 | 55% | 6 | 30% | 3 | 5% | 1 |
| 79% | 8 | 54% | 5 | 29% | 3 | 4% | 1 |
| 78% | 8 | 53% | 5 | 28% | 3 | 3% | 1 |
| 77% | 8 | 52% | 5 | 27% | 3 | 2% | 0 |
| 76% | 8 | 51% | 5 | 26% | 3 | 1% | 0 |
| | | | | | | 0% | 0 |

FIG. 8

| Restored | |
|---|---|
| Percentage of teeth with a restoration | Value |
| 100% | 9 |
| 99% | 9 |
| 98% | 9 |
| 97% | 9 |
| 96% | 9 |
| 95% | 9 |
| 94% | 9 |
| 93% | 9 |
| 92% | 9 |
| 91% | 9 |
| 90% | 9 |
| 89% | 9 |
| 88% | 9 |
| 87% | 9 |
| 86% | 9 |
| 85% | 9 |
| 84% | 9 |
| 83% | 9 |
| 82% | 9 |
| 81% | 9 |
| 80% | 9 |
| 79% | 9 |
| 78% | 9 |
| 77% | 9 |
| 76% | 9 |

| Restored | |
|---|---|
| Percentage of teeth with a restoration | Value |
| 75% | 8 |
| 74% | 8 |
| 73% | 8 |
| 72% | 8 |
| 71% | 8 |
| 70% | 8 |
| 69% | 8 |
| 68% | 8 |
| 67% | 8 |
| 66% | 8 |
| 65% | 7 |
| 64% | 7 |
| 63% | 7 |
| 62% | 7 |
| 61% | 7 |
| 60% | 7 |
| 59% | 7 |
| 58% | 7 |
| 57% | 7 |
| 56% | 7 |
| 55% | 7 |
| 54% | 6 |
| 53% | 6 |
| 52% | 6 |
| 51% | 6 |

| Restored | |
|---|---|
| Percentage of teeth with a restoration | Value |
| 50% | 6 |
| 49% | 6 |
| 48% | 6 |
| 47% | 6 |
| 46% | 6 |
| 45% | 6 |
| 44% | 6 |
| 43% | 5 |
| 42% | 5 |
| 41% | 5 |
| 40% | 5 |
| 39% | 5 |
| 38% | 5 |
| 37% | 5 |
| 36% | 5 |
| 35% | 5 |
| 34% | 5 |
| 33% | 4 |
| 32% | 4 |
| 31% | 4 |
| 30% | 4 |
| 29% | 4 |
| 28% | 4 |
| 27% | 4 |
| 26% | 4 |

| Restored | |
|---|---|
| Percentage of teeth with a restoration | Value |
| 25% | 4 |
| 24% | 4 |
| 23% | 4 |
| 22% | 3 |
| 21% | 3 |
| 20% | 3 |
| 19% | 3 |
| 18% | 3 |
| 17% | 3 |
| 16% | 3 |
| 15% | 3 |
| 14% | 3 |
| 13% | 3 |
| 12% | 3 |
| 11% | 2 |
| 10% | 2 |
| 9% | 2 |
| 8% | 2 |
| 7% | 2 |
| 6% | 2 |
| 5% | 2 |
| 4% | 2 |
| 3% | 2 |
| 2% | 1 |
| 1% | 1 |
| 0% | 1 |

FIG. 9

| Replace | |
|---|---|
| Percentage of teeth that should be replaced | Value |
| 100% | 9 |
| 99% | 9 |
| 98% | 9 |
| 97% | 9 |
| 96% | 9 |
| 95% | 9 |
| 94% | 9 |
| 93% | 9 |
| 92% | 9 |
| 91% | 9 |
| 90% | 9 |
| 89% | 9 |
| 88% | 9 |
| 87% | 9 |
| 86% | 9 |
| 85% | 9 |
| 84% | 9 |
| 83% | 9 |
| 82% | 9 |
| 81% | 9 |
| 80% | 9 |
| 79% | 8 |
| 78% | 8 |
| 77% | 8 |
| 76% | 8 |

| Replace | |
|---|---|
| Percentage of teeth that should be replaced | Value |
| 75% | 8 |
| 74% | 8 |
| 73% | 8 |
| 72% | 8 |
| 71% | 8 |
| 70% | 7 |
| 69% | 7 |
| 68% | 7 |
| 67% | 7 |
| 66% | 7 |
| 65% | 7 |
| 64% | 7 |
| 63% | 7 |
| 62% | 7 |
| 61% | 7 |
| 60% | 6 |
| 59% | 6 |
| 58% | 6 |
| 57% | 6 |
| 56% | 6 |
| 55% | 6 |
| 54% | 6 |
| 53% | 6 |
| 52% | 6 |
| 51% | 6 |

| Replace | |
|---|---|
| Percentage of teeth that should be replaced | Value |
| 50% | 5 |
| 49% | 5 |
| 48% | 5 |
| 47% | 5 |
| 46% | 5 |
| 45% | 5 |
| 44% | 5 |
| 43% | 5 |
| 42% | 5 |
| 41% | 5 |
| 40% | 4 |
| 39% | 4 |
| 38% | 4 |
| 37% | 4 |
| 36% | 4 |
| 35% | 4 |
| 34% | 4 |
| 33% | 4 |
| 32% | 4 |
| 31% | 4 |
| 30% | 4 |
| 29% | 3 |
| 28% | 3 |
| 27% | 3 |
| 26% | 3 |

| Replace | |
|---|---|
| Percentage of teeth that should be replaced | Value |
| 25% | 3 |
| 24% | 3 |
| 23% | 3 |
| 22% | 3 |
| 21% | 3 |
| 20% | 2 |
| 19% | 2 |
| 18% | 2 |
| 17% | 2 |
| 16% | 2 |
| 15% | 2 |
| 14% | 2 |
| 13% | 2 |
| 12% | 2 |
| 11% | 2 |
| 10% | 2 |
| 9% | 1 |
| 8% | 1 |
| 7% | 1 |
| 6% | 1 |
| 5% | 1 |
| 4% | 1 |
| 3% | 1 |
| 2% | 1 |
| 1% | 1 |
| 0% | 0 |

FIG. 11

DENTITION SCORE

BACKGROUND

Dental caries (e.g., tooth decay or cavities) is a disease that affects an individual tooth, which is repaired by restorative treatment when sufficient tooth structure remains to allow for such repair. When caries is sufficiently advanced, an affected tooth is extracted and, if desired, the dentition is repaired by prosthetic treatment that replaces the lost tooth with a prosthetic tooth. Severity is a term that can be used to describe the size of a carious lesion and extent can be used to describe the number of carious lesions in a dentition. In some examples, as shown in FIG. 1, severity can be defined as a linear extension by the depth of penetration from the outer tooth surface to the pulp. Dentist's use the carious lesion's severity to determine the type of treatment from the categories of preventative, restorative, or endodontic interventions. In some additional examples, severity can be defined by the three-dimensional configuration or volume of tooth structure destroyed, which dentist's use to determine if the tooth is restorable and the type of restoration indicated.

Dental caries is site-specific, which means that a dentition may have multiple independent sites of disease and multiple independent treatment interventions. Dentists often describe the status of the patient's dentition in very simple terms and from a perspective of treatment need using the number of teeth with caries and the number of teeth that need to be replaced. More sophisticated methods to describe a dentition have been developed for use in dental research but are not typically used for patient communication due to a lack of utility for this purpose. Existing dental indices include Decayed/Missing/Filled Teeth (DMFT), Decayed/Missing/Filled Surface (DMFS), Significant Caries Index (SiC), and Extrapolated Carious Surface Increment Index (ECSI).

DMFT describes the prevalence of teeth affected by dental caries in an individual. It is calculated by adding the number of decayed (D), missing (M), and filled (F) teeth (T). The score range is 0 to 28. The score and its component measures are sometimes used by public health organizations to determine dental status and treatment needs for a population. A DMFT score only increases and does not decrease with treatment. The only direction it can move is higher as the index increases with each tooth newly decayed or missing or filled.

DMFS differs from DMFT by substituting surfaces (S) for teeth (T), which results in a range of 0 to 128 for an adult. The SiC (Significant Caries Index) index is the mean DMFT of the one third of the study group with the highest caries score. The index can be used as a complement to the mean DMFT value.

ECSI (Extrapolated Carious Surface Increment Index) is a caries progression index, which takes into account the enlargement of existing lesions as well as the initiation of new ones.

SUMMARY

In some aspects, the dentition scores described herein can have clinical applicability for the individual patient. Since the score increases as a condition worsens and decreases with treatment, the score(s) can be used to communicate the status of a patient's dentition to the patient. Further, and unlike the scores described above, the described dentition scores will decrease as the patient's condition improves, thereby encouraging compliance both with restorative and preventive recommendations.

In some aspects, one or both of a caries score and a prosthetic score can be used to communicate dental health status to the patient. The prosthetic score is used to describe the individual's status with respect to missing teeth while the caries score describes the health (e.g., presence or absence of caries) for natural teeth. The caries score and prosthetic score can have one or more of the following features which provide the advantage of allowing the score to depict the status of an individual's teeth and dentition in a meaningful way. Each score is correlated to a unique set of clinical conditions in a linear manner. The score distinguishes natural health and deviations from natural health (restored health and disease) including the levels within each category where a lower score is indicative of improvement and a higher score denotes deterioration.

These characteristics are shared by the other communicative and universally adopted human descriptive scores, whether developed for health or otherwise. For example, most consumers are aware that their FICO credit score is an important number. If the consumer's credit is good, their FICO score is high, if it changes for the worse, the FICO score goes down, and consumers with the same scores will have very similar credit histories. Other examples of meaningful scores would include measurements for blood pressure, cholesterol, blood glucose, Body Mass Index, and the T score. The values associated with these entities have high utility for patients, and are also used to determine treatment needs, and the effectiveness of treatment interventions.

The caries score and the prosthetic score described herein for a dentition describe dental tooth health with a simple numeric score that is useful for communication of the status of the dentition. These scores can provide the advantage of improving the patient's understanding of their oral health condition, as well as enhancing the patient's participation in the management of their oral health, and/or improving the dentist's management of oral health services resulting in better health outcomes.

In some aspects, a method for describing a status of an individual's teeth over time includes generating one or both of a caries score and a prosthetic score. The caries score and the prosthetic score increase with increased need for treatment and decrease with effective treatment.

In some aspects, a method for describing a status of an individual's teeth over time includes classifying the teeth in an individual's dentition based on the status of each individual tooth. The method also includes classifying missing teeth in the individual's dentition based on the method of prosthetic tooth replacement. The method also includes determining a number of teeth in an individual's dentition that are optimal for the individual. The method also includes determining a number of teeth in an individual's dentition that are visible. The method also includes calculating, based on at least some of the classifications and determinations, a caries score associated with the extent of teeth in the individual's dentition affected by decay and calculating, based on at least some of the classifications and determinations, a prosthetic score associated with the status of the individual's dentition related to prosthetic tooth replacement. The caries score and the prosthetic score increase with increased need for treatment and decrease with effective treatment.

In some additional aspects, a method for generating a caries score for communicating the status of an individual's dentition includes retrieving a stored historical caries score for the individual and calculating a caries score based on a current status of the individual's dentition. The calculation generates an increased caries score with increased need and decreased caries score with effective treatment. The method also includes comparing the caries score to the historical caries score and communicating a change in the status of the individual's dentition based on the comparison of the caries score to the historical caries score where in increased score indicates a worsening condition and a decreased score indicates a decrease in need for treatment.

In some additional aspects, a method for generating a prosthetic score for communicating the status of an individual's dentition includes retrieving a stored historical prosthetic score for the individual. The method also includes calculating a prosthetic score based on a current status of the individual's dentition. The calculation generates an increased prosthetic score with increased need and decreased prosthetic score with effective treatment. The method also includes comparing the prosthetic score to the historical prosthetic score. The method also includes communicating a change in the status of the individual's dentition based on the comparison of the prosthetic score to the historical prosthetic score where in increased score indicates a worsening condition and a decreased score indicates a decrease in need for treatment.

Embodiments can include one or more of the following.

Classifying the teeth in an individual's dentition can include classifying each tooth in the individual's dentition as one or more of natural, carious, restored, or missing. Classifying the missing teeth in the individual's dentition can include classifying each missing tooth in the individual's dentition as one of a fixed prosthetic tooth, a removable prosthetic tooth, not replaced but needed for an optimal dentition, or not needed to be replaced for an optimal dentition.

An increasing caries score can be correlated to a worsening condition in which the individual's dentition includes an increased number of teeth in need of treatment and a decreasing caries score indicates successful treatment of carious lesions in the individual's dentition.

An increasing prosthetic score can be correlated to a worsening condition in which the individual's dentition includes an increased number of missing teeth that need to be replaced and a decreasing prosthetic score indicates successful replacement of needed missing teeth in the individual's dentition.

Removal of a carious tooth from the individual's dentition increases the individual's prosthetic score and decreases the individual's caries score.

The caries score can include a first digit associated with a percentage of teeth in the individual's dentition in need of treatment and a second digit associated with a percentage of teeth in the individual's dentition previously treated for a carious condition. The prosthetic score can include a first digit associated with the magnitude of need to replace teeth in the individual's dentition and a second digit associated with a percentage of prosthetic teeth that comprise a dentition that is optimal for the individual.

The method can also include storing the caries score and the prosthetic score, repeating, at a subsequent time, the classifying the teeth the an individual's dentition, calculating the caries score, and calculating the prosthetic score and generating a graph of the changes in the individual's caries score and prosthetic score over time.

Calculating the caries score can also include calculating a percentage of teeth in the individual's dentition with caries, calculating a percentage of teeth in the individual's dentition previously restored from a carious condition, determining a carious value for carious teeth based on the calculated percentage of teeth in the individual's dentition with caries, determining a restored value for restored teeth based on the calculated percentage of teeth in the individual's dentition previously restored from a carious condition, and determining the caries score based on the carious value and the restored value.

Calculating the prosthetic score can include determining a percentage of teeth in the individual's dentition in need of replacement, determining a value for tooth replacement, and calculating the prosthetic score based on the determined values.

The method can also include providing a table classifying potential caries scores into at least three classifications related to the health of the individual's dentition. The at least three classifications can include a first classification including a caries score associated with natural health of the dentition, a second classification including a first range of caries scores associated with previous carious conditions that have been fully restored, and a third classification including a second range of caries scores indicating existing disease and need for treatment.

The method can also include providing a table classifying potential prosthetic scores into at least three classifications related to the health of the individual's dentition. The at least three classifications can include a first classification including a prosthetic score associated with an optimal and natural health of the dentition, a second classification including a first range of prosthetic scores associated with previous tooth loss conditions that have been fully prosthetically repaired, and a third classification including a second range of prosthetic scores indicating existing tooth loss that is in need of prosthetic treatment.

DESCRIPTION OF DRAWINGS

FIG. 2 is a table of exemplary dentist observations and input data used to determine a prosthetic score and caries score.

FIG. 3 is a table of calculations used to determine the caries score and the prosthetic score.

FIG. 4 is a diagram of a primary dentition.

FIG. 5 is a diagram of a permanent dentition.

FIG. 6 is table of exemplary caries and prosthetic scores.

FIG. 8 is an exemplary caries look-up table.

FIG. 9 is an exemplary restored look-up table.

FIG. 11 is an exemplary lookup table used to determine a prosthetic score.

DESCRIPTION

Figure 1:
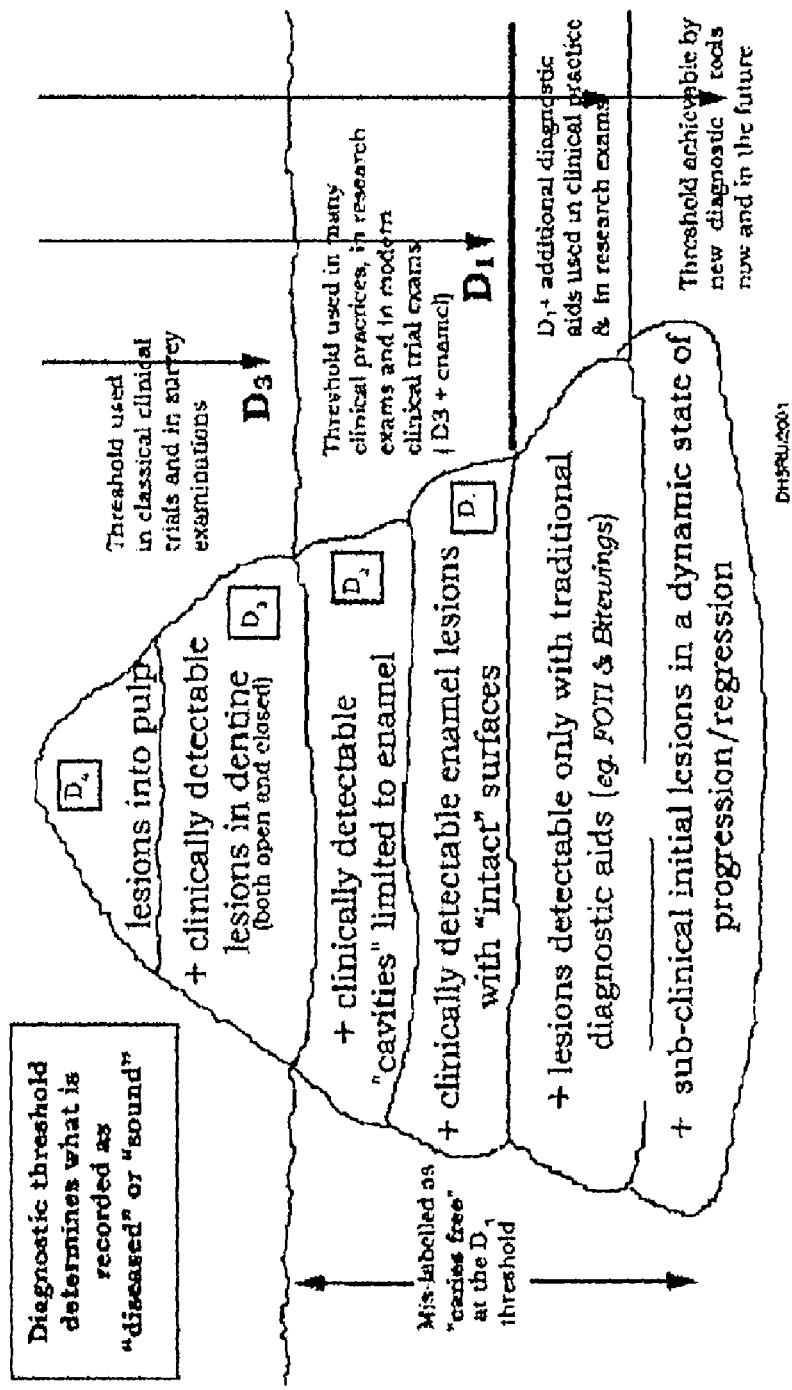
FIG. 1 is a diagram depicting a tooth and a severity measurement based on a depth of penetration from the outer tooth surface to the pulp.

Describing a dentition numerically presents specific challenges that stem from the need for the score to be able to describe the interrelated multi-state status of multiple entities (e.g., teeth). For example, people have only one blood sugar level, one credit score, but most individuals start adult life with 28 teeth. A tooth may be described by one of the following states—natural, restored, carious, or missing where the prosthetic replacement may be by means of a removable denture, fixed bridge, or implant. A simple solution to eliminate caries by replacing all natural teeth with prosthetic teeth would not be understood by the average consumer as the equivalent of a full dentition with no decay or health. The dentition score addresses this challenge by providing two separate scores, a caries score and a prosthetic score, that together comprise the overall status of the dentition and are referred to as a dentition score. The caries score and prosthetic score are both numerical scores. For example, a 1-100 score can be used for the caries score and a separate 1-100 score can be for the prosthetic score. Both the caries score and the prosthetic score increase with increased need and decrease with effective treatment.

The caries score is associated with the status of teeth in the individual's dentition affected by decay and the prosthetic score is associated with the status of the individual's dentition related to prosthetic tooth replacement. Together the caries score and the prosthetic score can provide an understanding of the health of the dentition. For example, if a patient had rampant caries and no replaced teeth, the caries score would be high and the prosthetic score low. If another patient had only a few teeth where these teeth never had caries and no prosthetic teeth were ever made, the caries score would be low and the prosthetic score high.

The use of multiple scores to describe an aspect of health has precedence as blood pressure includes systolic and diastolic and cholesterol includes HDL and LDL. Similarly, the dentition score includes the caries and prosthetic scores that together describe two related and interdependent components of the dentition. The caries score describes the dentition in terms of the visible teeth affected by decay (e.g., caries and restored teeth). The caries score is a measure of extent and does not include a measure for severity (depth of lesions encountered). A restored tooth is defined as a tooth that has a filling or cap (crown). A caries score of 1 means that the visible teeth have never had decay or been restored. Scores from 2 to 9 mean that all of the visible teeth that had decay have been restored where higher scores correlate to a larger percentage of restored teeth. Scores within the range of 10 to 100 mean that decay exists and restorative treatment is needed where higher scores correspond to more severe conditions and higher restorative treatment need. For scores 10 to 99 the ten's digit reflects the increasing percentage of carious teeth and the unit's digit is the increasing percentage of restored teeth. A score of 100 represents the most severe condition and highest need. The caries score will decrease upon the completion of all needed treatment to a score in the 2 to 9 range based on the percentage of restored teeth. Furthermore, a tooth that is extracted as an alternative to restorative treatment will be captured by the prosthetic score.

By using both caries and prosthetic scores to describe a dentition's status a decrease in the caries score that results from tooth extraction will result in an increase in the prosthetic score. The prosthetic score describes the status of the dentition in terms of prosthetic tooth replacement, which typically is not a treatment intervention that is needed prior to the age of 19 years. Tooth replacement includes removable appliances (e.g., partial and full dentures), non-removable appliances (e.g., bridges), and single tooth replacement implants. A prosthetic score of 1 means that the dentition has the optimal number of natural teeth. Scores from 2 to 9 mean that the dentition has been completely repaired with higher scores indicative of a larger percentage of teeth that needed to be replaced to achieve a dentition that is optimal for the patient. Scores within the range of 10 to 100 mean that prosthetic treatment is needed. Higher prosthetic scores correspond to more severe conditions and higher prosthetic treatment need. For scores 10 to 99, the ten's digit reflects the increasing severity of tooth loss and the unit's digit is the increasing magnitude of current tooth replacement need. A score of 100 represents the most severe condition and highest need. The prosthetic score will decrease upon the completion of all needed treatment to a score in the 2 to 9 range based on the percentage of teeth that needed to be replaced.

Future treatment needs for the dentition may be determined from the caries score and prosthetic score. These scores are calculated from a limited number of the dentist's observations that are first input into the system (FIG. 2) whereupon the system performs calculations using the input data (FIG. 3). For example, a dentist can make the needed observations and enter the observations into a computer system which stores the entered values and uses one or more algorithms to perform the calculations used to determine the caries and prosthetic scores.

As shown in FIG. 2, the inputs to the system based on the dentist's observations include an input 100 indicating how many teeth are optimal for the patient excluding third molars, an input 102 of how many natural teeth are visible excluding third molars, an input 104 of how many teeth have any type of restoration including crowns and veneers, and input 106 of how many teeth have caries or defective restoration, and input 108 of how many teeth that have been replaced that are not removable by the patient, and in input 110 of how many teeth that have been replaces that are removable by the patient. In some embodiments, additional inputs may be used to supplement these inputs.

As described above, the system performs calculations using the inputs 100, 102, 104, 106, 108, and 110. As shown in FIG. 3, these calculations can include calculation of a percentage 120 of teeth with caries, a percentage 122 of teeth with a restoration, a value 124 for carious teeth, a value 126 for restored teeth, a number 128 of teeth that should be replaced, a percentage 130 of optimal teeth that should be replaced, a value 132 for tooth replacement, and a value 134 for missing teeth that need to be replaced. In some embodiments, additional calculations may be used to supplement these calculated values. The calculated values 120, 122, 124, 126, 128, 130, 132, and 134 are used to determine the caries score and prosthetic score for an individual (e.g., as described herein).

A risk score for caries determined by a caries risk calculator (e.g., available at the PreViser website) supplements the caries and prosthetic scores so that a complete picture of current and potential needs can be determined. For example, the need and probable cost for future restorative treatment may be determined from the risk for caries and the caries score. Such needs may include restoration of new carious lesions, or replacement of existing restorations which is eventually necessary since every restoration uses materials that have a limited life. The need and probable cost for future prosthetic treatment may be determined from a consideration of the prosthetic score, the caries score and the risk for caries. Elements of this analysis include: 1) the number of prosthetically replaced teeth since every prosthesis uses materials that have a limited life, 2) the number of teeth with a restoration since extraction may be needed when the restoration fails (e.g., restoration or tooth fracture), and 3) caries risk since extraction may be needed when caries is severe. In some examples, an insurance carrier can evaluate the caries score and the prosthetic score when determining a rate and/or deductible to offer for dental insurance for an individual. In some additional examples, an insurance carrier can evaluate mean and/or median caries scores and the prosthetic scores for a cross-section of individuals with similar characteristics (e.g., a particular age range, income level, location, etc) and use the information for when determining a rate and/or deductibles to offer for dental insurance for a particular group of individuals. By viewing the caries scores and prosthetic scores, the insurance carrier can determine an expected cost based on the likelihood of individuals.

Teeth first appear in the mouth around the 6$^{th}$ month of life. By the 3$^{rd}$ year all of the primary teeth have erupted where 20 primary teeth comprise the dentition (e.g., as shown in FIG. 4). Between 6 months and 3 years the number of visible teeth increases from 1 to 20. At approximately the age of 6 years the first permanent tooth erupts behind (e.g., distal) the primary second molars increasing the number of visible teeth to 24 (e.g., as shown in FIG. 5). Between the age of 6 and 12, the primary teeth are shed with the permanent teeth erupting into the vacated spaces. During this period the dentition is comprised of a decreasing number of primary teeth and an increasing number of permanent teeth. During the process of shedding and eruption, the number of visible teeth will fall and rise. By the age of 13 years, all of the primary teeth have been replaced with permanent teeth and the permanent second molars have erupted bringing the total number of teeth in an adult dentition to 28. The four third molars (e.g., wisdom teeth) may be congenitally absent, they may fail to erupt (e.g., remain impacted), or they may erupt into the dentition. These four teeth typically are not needed and they are frequently extracted. Sometimes the teeth are too large for the size of the jaw resulting in crowding and misalignment, which is frequently treated with a combination of selectively extracting certain teeth (e.g., four first premolars) and aligning the remaining teeth with orthodontic appliances. Hence the optimal number of teeth for a specific patient's dentition varies with patient age and jaw size. While the optimal number of teeth for most adults is 28, 24 or fewer are optimal for some adults. After the age of 19 years, loss of teeth due to disease may occur resulting in the number of visible teeth being less than the number of teeth that are optimal for the patient.

Upon eruption of a tooth into the mouth, dental caries becomes possible. Dental caries is a disease that affects a tooth, which may be repaired by restorative treatment when possible. When the loss of tooth structure is severe because of caries or fracture, the tooth is extracted resulting in a suboptimal dentition which may be repaired by prosthetic treatment. Therefore a description of a dentition requires independent descriptions of the status of the individual teeth and the collective group of teeth. The caries score describes the dentition in terms of the visible teeth affected by decay (e.g., caries and restored teeth). The prosthetic score describes the status of the dentition in terms of prosthetic tooth replacement. The scores are calculated using the clinical observations of a dentist made during the examination of a patient (e.g., using the observations described above in relation to FIG. 2).

FIG. 6 shows different examples of the calculation of the caries score (shown in column 140) and prosthetic score (shown in column 142). For example, patient A in FIG. 6 is a 52-year old male. During an examination the dentist observes that 27 teeth are visible in jaws that optimally could accommodate 28 teeth, 5 of the visible teeth have a restoration where 2 teeth are restored with crowns that serve as abutments for a bridge and 3 teeth have a filling. The filled teeth include the upper left second molar, the upper left first premolar, and the lower right first premolar. Caries exists for the upper left second molar and lower right first premolar. The missing tooth, the upper right first molar, has been replaced with a 3-unit fixed bridge where abutment crowns exist for the upper right second molar and second premolar and the missing first molar is replaced with a fixed prosthetic tooth. Therefore, the dentition includes 1 fixed prosthetic tooth.

Figure 7:
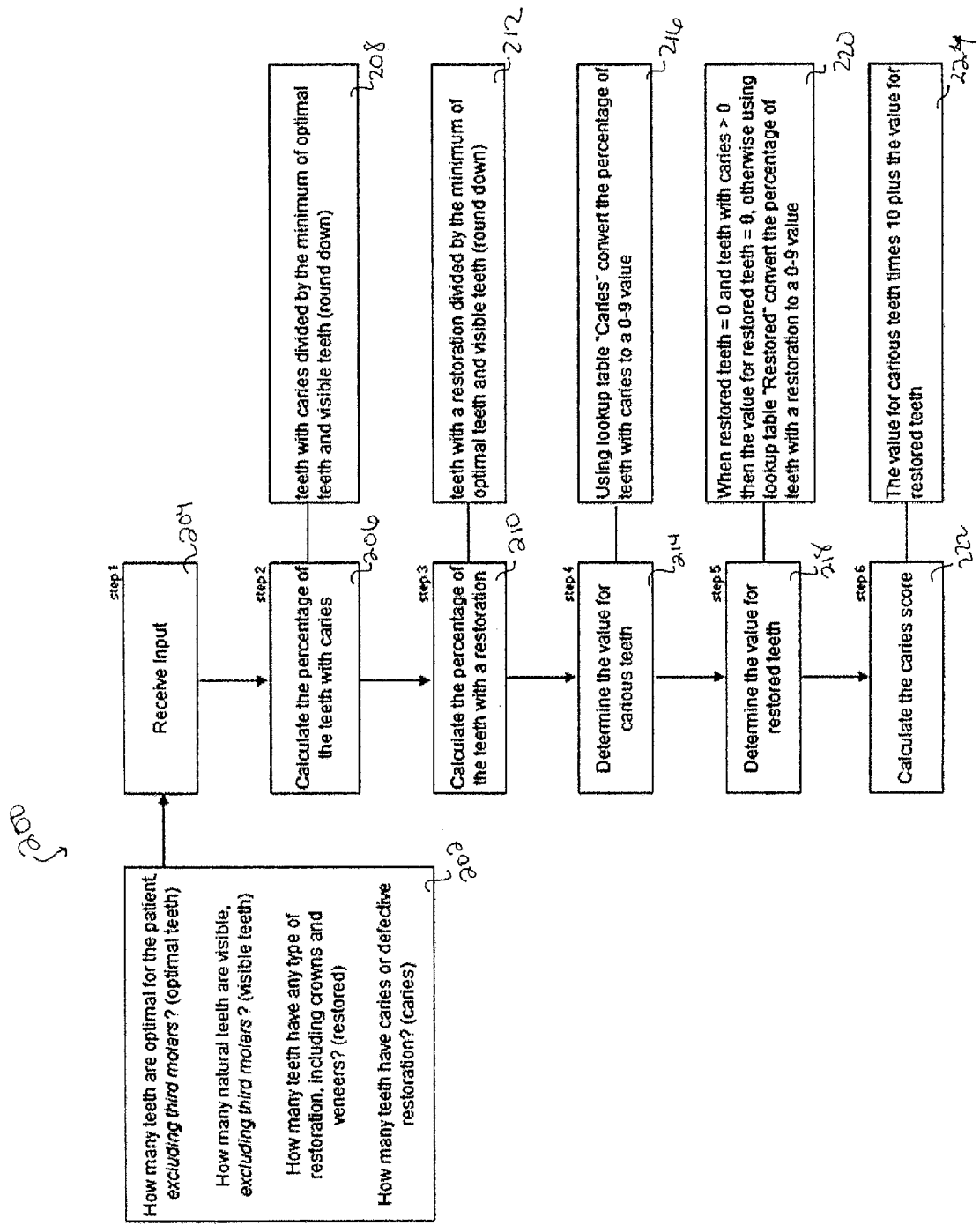
FIG. 7 is a flow chart for a method of determining a caries score.

Referring to FIG. 7, a process 200 for calculating the caries score is shown. The calculation of the caries score includes determining the values used to calculate the caries score including how many teeth are optimal for the patient, how many natural teeth are visible, how many teeth have any type of restoration, and how many teeth have caries or defective restoration (202). These four values are typically determined by a dentist or other dental care professional. The four values required to calculate the caries score are input into the system (204).

After the inputs are received, the system calculates the percentage of teeth with caries (206). As shown in block 208, the percentage of teeth with caries can be calculated by dividing the number of teeth with caries by the minimum of the optimal number of teeth and visible teeth. The percentage is rounded down to the nearest integer to yield the percentage of teeth with caries. The system also calculates the percentage of teeth with a restoration (210). As shown in block 212, the percentage of teeth with a restoration is calculated by dividing the number of teeth with a restoration by the minimum of the optimal number of teeth and visible teeth. The percentage is rounded down to the nearest integer. The system also looks up the value for carious teeth (214). As shown in block 216, this is done by finding the value for the percentage of teeth with caries using a look-up table.

An exemplary Caries Look-up Table is shown in FIG. 8. In the Caries Look-up Table shown in FIG. 8, the left column of the Caries Look-up Table includes the percentage of teeth with caries, and the right hand column includes the associated value for carious teeth. The system also determines the value for restored teeth (218). As shown in block 220, a Restored Look-up Table is conditionally used to convert the percentage of teeth with a restoration to a 0 to 9 value for restored teeth. The Restored Look-up Table is used when the number of restored teeth >0 or no teeth have a restoration or caries. The Restored Look-up Table is not used when the number of restored teeth=0 and teeth with caries >0. When this condition exists the value for restored teeth is 0.

An exemplary, Restored Look-up Table is shown in FIG. 9. Using the Restored Look-up Table (FIG. 9), the percentage of teeth with a restoration is found in the left column where the value for restored teeth is in the right column of the same row. The system calculates the caries score (222) by multiplying the value for carious teeth by 10 and adding the value for the restored teeth (as described in block 224).

Referring back to FIG. 6, In the example described above, a value of 28 is entered for the number of optimal teeth (as shown in FIG. 6, column 100), a value of 27 is entered for the number of visible teeth (as shown in FIG. 6, column 102), a value of 5 is entered for the number of restored teeth (as shown in FIG. 6, column 104), and a value of 2 is entered for the number of teeth with caries or defective restoration (as shown in FIG. 6, column 106).

After the inputs are received, the system calculates the percentage of teeth with caries by dividing 2, the number of teeth with caries (206), by 27, the minimum of the optimal number of teeth (e.g., 28) and visible teeth (e.g., 27). The percentage is rounded down to the nearest integer to yield 7% (FIG. 6, column 120). The system calculates the percentage of teeth with a restoration (210) by dividing 5, the number of teeth with a restoration by 27, the minimum of the optimal number of teeth and visible teeth. The percentage is rounded down to the nearest integer to yield 18% (FIG. 6, column 122). The system looks up the value for carious teeth (214). This is done by finding 7%, the value for the percentage of teeth with caries, in the left column of the Caries Look-up Table (FIG. 8) where the value for carious teeth, 1, is in the right column of the same row (FIG. 6, column 124).

The system determines the value for restored teeth (218). Since there are five restored teeth, the Restored Look-up Table (FIG. 9) is used to convert the percentage of teeth with a restoration to a 0 to 9 value for restored teeth. Using the Restored Look-up Table (FIG. 9), the percentage of teeth with a restoration, 18% is found in the left column where the value for restored teeth, 3, is in the right column of the same row (FIG. 6, column 126). The caries score is calculated (222) by multiplying the value for carious teeth, 1, by 10 and adding the value for the restored teeth, 3, to yield 13 (FIG. 6, column 140).

Figure 10A:
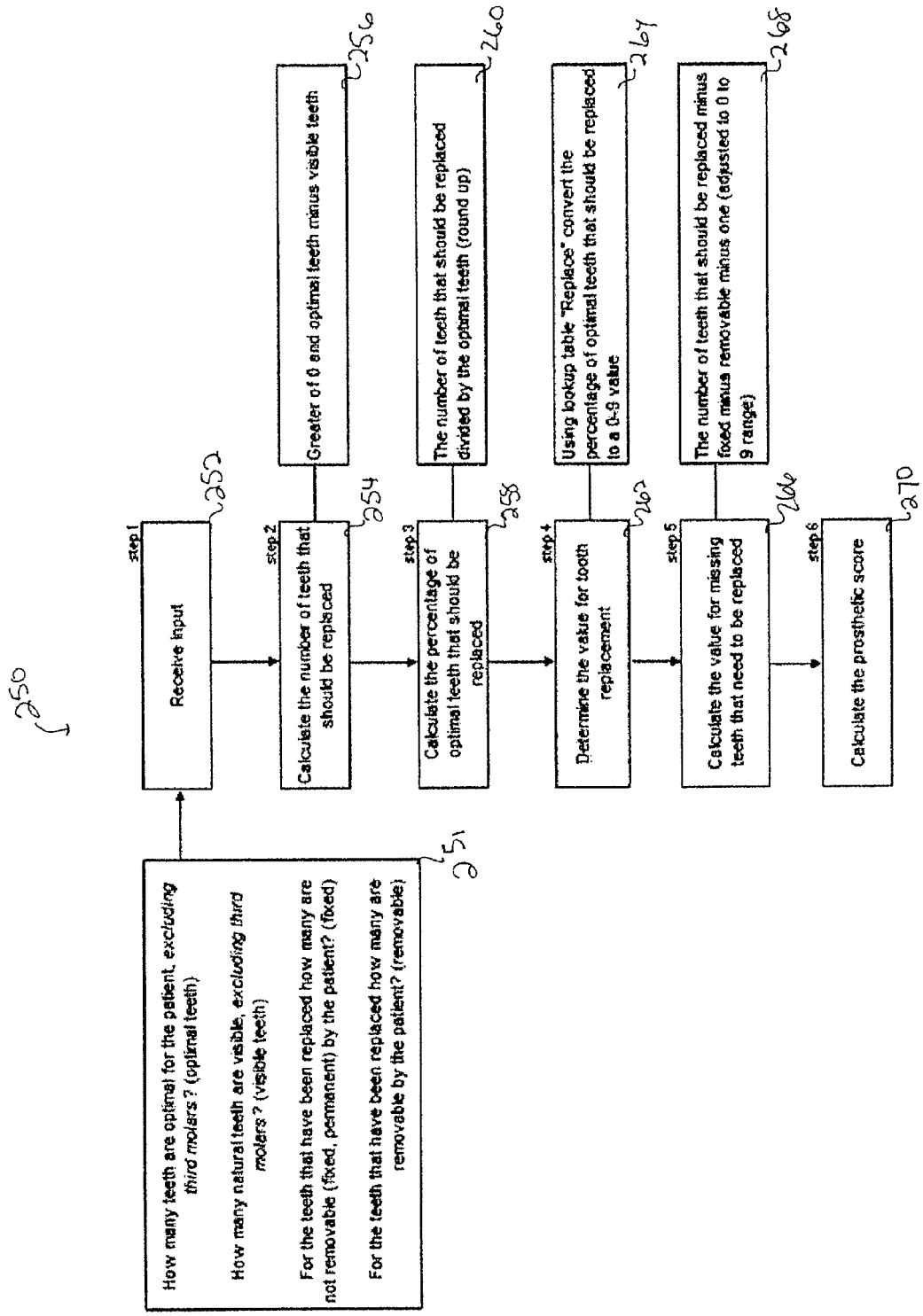
FIG. 10A is a flow chart for a method of determining a prosthetic Score.

Referring to FIG. 10A, a process 250 for calculating the prosthetic score is shown. The four values required to calculate the prosthetic score (e.g., as shown in block 251) are input into the system (252). The values that are input include the number of optimal teeth, the number of visible teeth, the number of teeth that have been replaced that are not removable by the patient, and the number of teeth that have been replaced that are removable by the patient. The system calculates the number of teeth that should be replaced (254). As shown in block 256, number of teeth that should be replaced can be calculated by subtracting the number of visible teeth from the number of optimal teeth and using the greater of this difference and 0. The system calculates the percentage of optimal teeth that should be replaced (258). As shown in block 260, the percentage of optimal teeth that should be replaced is calculated by dividing the number of teeth that should be replaced by the optimal number of teeth. The percentage is rounded up to the nearest integer.

The system looks up the value for tooth replacement (262). As shown in block 264, this is done by finding the percentage of optimal teeth that should be replaced, in the left column of the Replace Look-up Table (FIG. 11), with the value for tooth replacement in the right column of the same row. The system calculates the value for missing teeth that need to be replaced (266). As shown in block 268, the value for missing teeth that need to be replaced is calculated by subtracting the fixed prosthetic teeth and the removable prosthetic teeth from the number of teeth that should be replaced. 1 is subtracted from this difference. If the value is negative it is adjusted to 0 and if the value exceeds 9 it is adjusted to 9, as the range must be in the range of 0 to 9. The system uses the values of process 250 to complete the calculation of the prosthetic score (270).

Figure 10B:
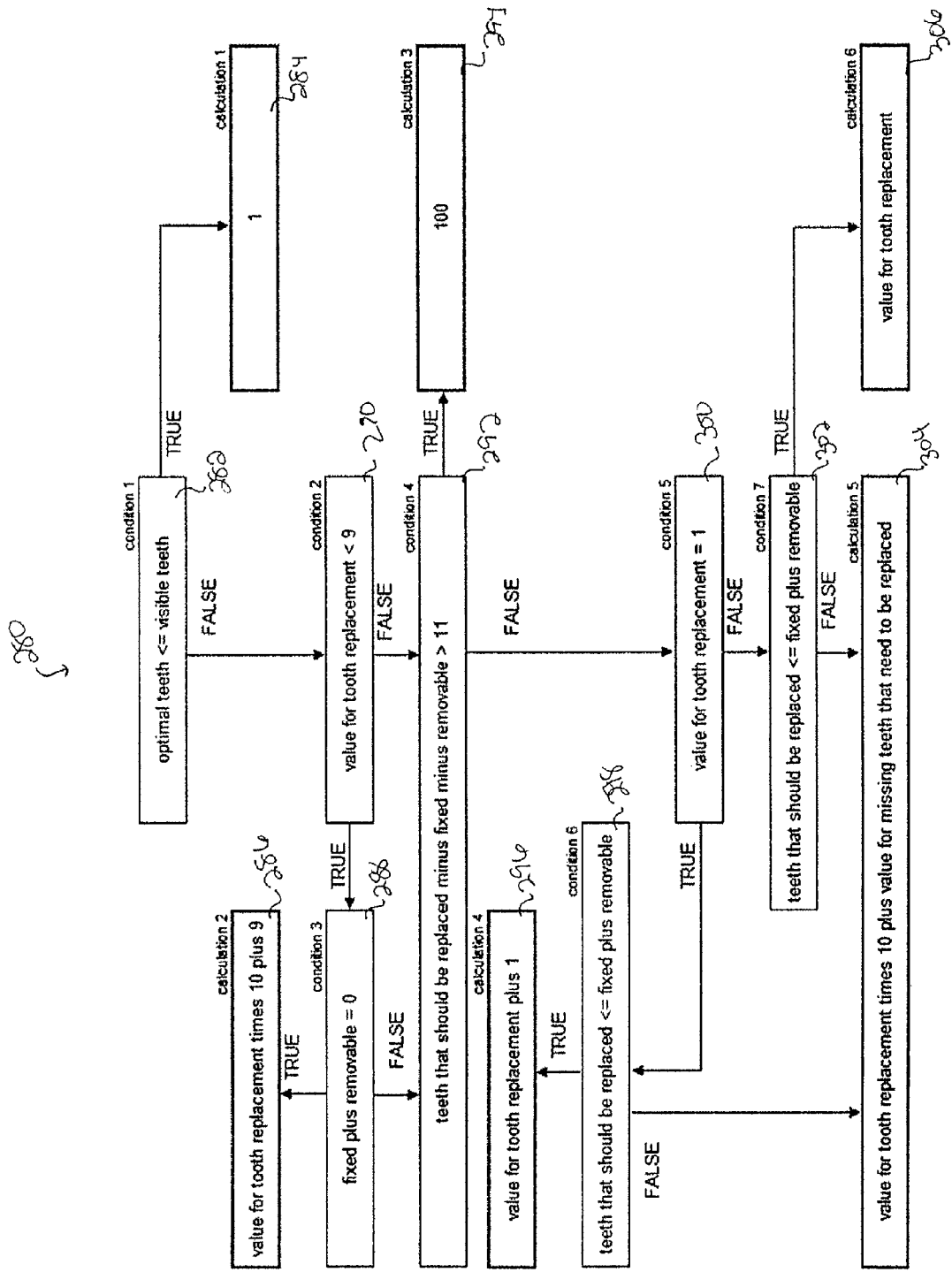
FIG. 10B is a flow chart of a method for determining a prosthetic score.

The prosthetic score can be calculated using process 280 shown in FIG. 10B. The system determines if the number of optimal teeth is less than or equal to the number of visible teeth (condition 1) (282). If the number of optimal teeth is less than or equal to the number of visible teeth, the prosthetic score is 1 (calculation 1) (block 284). If the number of optimal teeth is greater than the number of visible teeth, the system determines if the value for tooth replacement is less than 9 (condition 2) (block 290). If the value for tooth replacement is less than 9, the system proceeds to determining if condition 3 (block 288) is true or false. If the value for tooth replacement is greater than or equal to 9, the system proceeds to determining if condition 4 (block 292) is true or false.

From the determination of condition 3, if condition 3 (block 288) is true, the prosthetic score is calculated using calculation 2, which is the value for tooth replacement times 10 plus 9 (286). From the determination of condition 3, if condition 3 (block 288) is false, the system proceeds to determining if condition 4 (block 292) is true or false.

From the determination of condition 4, if condition 4 (block 292) is true, the prosthetic score is 100 (calculation 3) (294). From the determination of condition 4, if condition 4 (block 292) is false, the system proceeds to determining if condition 5 (block 300) is true or false.

From the determination of condition 5, if condition 5 (block 300) is true, the system proceeds to determining if condition 6 (block 298) is true or false. From the determination of condition 5, if condition 5 (block 300) is false, the system proceeds to determining if condition 7 (block 302) is true or false.

From the determination of condition 6, if condition 6 (block 298) is true, the prosthetic score is calculated using calculation 4, which is the value for tooth replacement plus 1 (296). From the determination of condition 6, if condition 6 (block 298) is false, the prosthetic score is calculated using calculation 5, which is the value for tooth replacement times 10 plus the value for missing teeth that need to be replaced (304).

From the determination of condition 7, if condition 7 (block 302) is true, the prosthetic score is calculated using calculation 6, which is the value for tooth replacement (306). From the determination of condition 7, if condition 7 (block 302) is false, the prosthetic score is calculated using calculation 5, which is the value for tooth replacement times 10 plus the value for missing teeth that need to be replaced (304).

The calculation of the prosthetic score is explained using example 1 in FIG. 6. Referring to FIG. 10A, the four values required to calculate the prosthetic score are input into the system (252); 28 for the number of optimal teeth (FIG. 6, column 100), 27 for the number of visible teeth (FIG. 6, column 102), 1 for the number of teeth that have been replaced that are not removable by the patient (FIG. 6, column 108), and 0 for the number of teeth that have been replaced that are removable by the patient (FIG. 6, column 110). The system calculates (254) the number of teeth that should be replaced by subtracting the number of visible teeth, 27, from the number of optimal teeth, 28, and using the greater of this difference and 0 yielding 1 (FIG. 6, column 128). The system calculates (258) the percentage of optimal teeth that should be replaced by dividing 1, the number of teeth that should be replaced, by 28, the optimal number of teeth. The percentage is rounded up to the nearest integer to yield 4% (FIG. 6, column 130). The system looks up the value for tooth replacement (262). This is done by finding 4%, the percentage of optimal teeth that should be replaced, in the left column of the Replace Look-up Table (FIG. 11), with the value for tooth replacement, 1, in the right column of the same row (FIG. 6, column 132). Step 5 calculates the value for missing teeth that need to be replaced by subtracting 1, the fixed prosthetic teeth, and 0, the removable prosthetic teeth, from 1, the number of teeth that should be replaced. 1 is subtracted from this difference and the value, −1 (negative 1), is adjusted to 0 (FIG. 6, column 134), as the range must be 0 to 9. The next series of steps is explained using FIG. 10B. Since the number of optimal teeth, 28, is greater than the number of visible teeth, 27, condition 1 is false. The next step, condition 2, is whether the value for tooth replacement is less than 9. This is true, since the value is 1 (FIG. 6, column 132). The next step, condition 3, is whether the number of fixed plus removable prosthetic teeth is 0. This condition is false, since the sum is 1 (e.g., fixed=1, removable=0). The next step, condition 4, is whether the number of teeth that should be replaced minus the fixed and removable prosthetic teeth is greater than 11. This is false since 1, the number of teeth that should be replaced, minus 1, the number of fixed prosthetic teeth, minus 0, the number of removable prosthetic teeth, yields 0. The next step, condition 5, is whether the value for tooth replacement equals 1 (FIG. 6, column 132). This is true. The next step, condition 6, is whether the number of teeth that should be replaced is less than or equal to the number of fixed plus removable prosthetic teeth. This is true, as the number of teeth that should be replaced is 1 (FIG. 6, column 128) and the number of fixed plus removable prosthetic teeth is 1. Based on these conditions, the prosthetic score uses calculation 4, the value for tooth replacement, 1, (FIG. 6, column 132) plus 1 to yield 2 (FIG. 6, column 142).

The method of calculation of the scores and their utility can be explained using the other examples in FIG. 6. The second example is also for patient A, which describes the patient's revised dental status following treatment. Treatment applied for the two teeth with carious lesions included extraction of the upper left second molar and a new restoration for the lower right first premolar. The new values and scores following treatment are: 28 optimal teeth, 26 visible teeth (e.g., the upper second molar was extracted reducing the number of visible teeth from 27 to 26), 4 restored teeth (e.g., the restored upper second molar was extracted reducing the number of restored teeth from 5 to 4 and the re-restoration of the lower right first premolar results in no net change in restored teeth), 0 carious teeth (e.g., all carious lesions were treated), 1 fixed prosthetic tooth, and 0 removable prosthetic teeth. As a result of treatment the caries score is reduced from 10 to 3, which is indicative of a fully restored condition. The prosthetic score is 10, which is indicative that prosthetic tooth replacement for the extracted upper second molar is needed.

The prosthetic score is determined using the input and calculated values following the method of FIG. 10A and applied in the logic tree of FIG. 10B. These values include: 28 optimal teeth, 26 visible teeth, 1 fixed prosthetic tooth, 0 removable prosthetic teeth, 2 teeth that should be replaced, 7% for the percentage of optimal teeth that should be replaced, value for tooth replacement is 1, and the value for missing teeth that need to be replaced is 0. Since the number of optimal teeth, 28, is greater than the number of visible teeth, 26, condition 1 is false. Condition 2 is true, since the value for tooth replacement is 1. Condition 3 is false, since the number of fixed plus removable prosthetic teeth is 1. Condition 4 is false since the number of teeth that should be replaced minus the fixed and removable prosthetic teeth is 1. Condition 5 is true since the value for tooth replacement is 1. Condition 6 is false, since the number of teeth that should be replaced, 2, is greater than 1, the number of fixed plus removable prosthetic teeth. Based on these conditions, the prosthetic score uses calculation 5, the value for tooth replacement, 1, multiplied by 10 plus 0, the value for missing teeth that need to be replaced to yield 10.

In example 2 the optimal number of teeth is 28. When the upper second molar is not needed, as may occur for some patients, then the number of optimal teeth would be 27 instead of 28. Hence if patient A did not need the upper second molar, then the prosthetic score would be 2 as shown in example 3. In this situation the dentition is repaired to an optimal state and no prosthetic treatment is needed.

Sometimes the teeth are too large for the size of the jaw resulting in crowding and misalignment, which is frequently treated with a combination of selectively extracting certain teeth (e.g., four first premolars) and aligning the remaining teeth with orthodontic appliances where the optimal number of teeth is 24. FIG. 6 includes this situation described for patient B, example 4. In this example the dentist has observed that 24 teeth are visible, 8 have been restored, and no tooth has caries. The caries score for this condition is 4 and the prosthetic score is 1 (e.g., from FIG. 10B, condition 1 is true, calculation 1). During a subsequent examination, patient B develops caries in 2 un-restored teeth and 1 restored tooth, as shown in example 5. The three new carious lesions results in an increase in the caries score from 4 to 24, indicative of treatment need. When restorative treatment is completed, as shown in example 6, the caries score will decrease to 5. Since treatment included restoring two teeth previously not restored, the number of restored teeth increased from 8 to 10 resulting in the caries score to increase from 4 to 5 as can be seen by comparing example 4 with example 6.

Prosthetic tooth replacement may be categorized as removable, non-removable, and single tooth replacement implants. Removable prostheses include partial and full dentures. While an abutment tooth for a removable partial denture may be utilized, the tooth may or may not be restored. However, a bridge, which is a non-removable prosthesis, commonly requires a crown (e.g., restoration) for each abutment tooth. The replacement of a single missing tooth with a bridge typically includes a crown for each of two abutment teeth and one (fixed) prosthetic tooth. The replacement of a single missing tooth can be accomplished without the need for a crown for any visible teeth by utilizing a single tooth replacement implant. The combination of caries and prosthetic scores can capture the difference between a bridge and implant.

FIG. 6 includes patient C where example 7 is the situation where each of two missing teeth is replaced with a 3-unit fixed bridge. For example 7, a crown for each of the 4 abutment teeth is required to replace the two missing teeth. This results in 3 for the caries score and 2 for the prosthetic score. In example 8 the two missing teeth are replaced using the single tooth replacement method (e.g., 2 single implants each restored with a crown). Since no natural teeth need to be restored for this method, the caries and prosthetic scores are 1 and 2, respectively. In both situations the dentition is repaired to an equivalent optimal status. However, the use of crowns in example 7 by virtue of four crowns is not equivalent to the never diseased or restored dentition in example 8. While the caries and prosthetic scores cannot differentiate between fixed and removable prosthetic teeth, these independent observations could be used as a means of differentiation for prosthetically repaired dentitions.

A patient may be at very high risk for caries and have many restored teeth. FIG. 6 includes patient D who represents this situation. Example 9 describes the situation where all 28 teeth needed for an optimal dentition are present, 22 teeth have been restored, and 6 of the restorations are defective with caries. The caries and prosthetic scores for this situation are 29 and 1, respectively. Should the patient elect to extract the 6 teeth with caries, the caries score would reduce to 8 but the prosthetic score would increase to 39 (e.g., from FIG. 10B, condition 1 is false, condition 2 is true, condition 3 is true, calculation 2 is used), as shown in example 10. However, replacement of the 6 teeth with a removable partial denture, example 11, would reduce the prosthetic score to 3 (FIG. 10B, calculation 6). Examples 9, 10, and 11, highlight the use of the scores to document: 1) treatment need where the examples include 29 for a caries score and 39 for prosthetic score; 2) completion of needed treatment where the examples include a reduction in the caries score from 29 to 8 and prosthetic score from 39 to 3. This set of examples also shows that merely extracting teeth to reduce the caries score (e.g., 29 to 8) will result in an increase in the prosthetic score (e.g., 1 to 39). And furthermore, example 11 shows that with prosthetic treatment, the prosthetic score will be higher than the score for the original condition listed in example 9 (e.g., 3 versus 1).

An adolescent may be temporarily missing teeth as permanent teeth do not instantaneously erupt to take the place of primary teeth as they are shed. Prosthetic tooth replacement is typically not needed prior to the age of 19. Hence the concept of an optimal number of teeth and the prosthetic score are not applicable until the age of 19 is attained. The caries score describes the dentition in terms of the visible teeth affected by decay and therefore is applicable when the dentition is comprised of only primary teeth, primary and permanent teeth, and only permanent teeth. FIG. 6 includes patient E, a 10-year-old female who has 14 primary and 10 secondary teeth. At the initial examination, listed in example 12, 6 of the primary teeth have a restoration and 2 of the permanent teeth have caries, which results in a caries score of 14. Immediately following treatment where both carious lesions are restored, the caries score is reduced to 4. Three years later when the natural eruptive process results in the addition of the permanent second molars and the replacement of the primary teeth with never-carious and never-restored permanent teeth, the caries score is reduced to 2.

The system, e.g., the system used to calculate the caries and prosthetic scores and methods described herein can be implemented in digital electronic circuitry, or in computer hardware, firmware, software, web-enabled applications, or in combinations thereof. Data structures used to represent information about an individual's dentition can be stored in memory and in persistence storage. Apparatus of the invention can be implemented in a computer program product tangibly embodied in a machine-readable storage device for execution by a programmable processor and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired, and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files, such devices include magnetic disks, such as internal hard disks and removable disks magneto-optical disks and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

What is claimed is:

1. A method for describing a status of an individual's teeth over time, the method comprising:
   receiving, by a computer system configured to calculate a caries score and a prosthetic score based on at least a stored look-up table, a classification of the teeth in an individual's dentition indicative of a status of each individual tooth;
   determining, by the computer system configured to calculate the caries score and the prosthetic score, based on the classifications based on the status of each individual tooth, a number of teeth in the individual's dentition having caries or a defective restoration;
   receiving, by the computer system configured to calculate the caries score and the prosthetic score, a classification of missing teeth in the individual's dentition based on a method of prosthetic tooth replacement, the classifications providing information for determining a number of teeth that have been replaced and are removable and a number of teeth that have been replaced and are not removable;
   calculating, by the computer system configured to calculate the caries score and the prosthetic score, based on at least a number of teeth that are optimal for the individual, a number of teeth in the individual's dentition that are visible, a number of teeth with restoration, and the number of teeth having caries or a defective restoration, the caries score associated with the extent of teeth in the individual's dentition affected by decay; and
   calculating, by the computer system configured to calculate the caries score and the prosthetic score, based on at least the number of teeth that are optimal for the individual, the number of teeth in the individual's dentition that are visible, the number of teeth that have been replaced mad are removable and the number of teeth that have been replaced and are not removable, the prosthetic score associated with the status of the individual's dentition related to prosthetic tooth replacement, the prosthetic score being different than the caries score;
   wherein the caries score and the prosthetic score each increase with increased need for treatment and decrease with effective treatment.

2. The method of claim 1, wherein classifying the teeth in an individual's dentition comprises classifying each tooth in the individual's dentition as one or more of natural, carious, restored, or missing.

3. The method of claim 1, wherein classifying the missing teeth in the individual's dentition comprises classifying each missing tooth in the individual's dentition as one of a fixed prosthetic tooth, a removable prosthetic tooth, not replaced but needed for an optimal dentition, or not needed to be replaced for an optimal dentition.

4. The method of claim 1, wherein an increasing caries score is correlated to a worsening condition in which the individual's dentition includes an increased number of teeth in need of treatment; and
   a decreasing caries score indicates successful treatment of carious lesions in the individual's dentition.

5. The method of claim 1, wherein:
   an increasing prosthetic score is correlated to a worsening condition in which the individual's dentition includes an increased number of missing teeth that need to be replaced; and
   a decreasing prosthetic score indicates successful replacement of needed missing teeth in the individual's dentition.

6. The method of claim 1, wherein removal of a carious tooth from the individual's dentition increases the individual's prosthetic score and decreases the individual's caries score.

7. The method of claim 1, wherein the caries score includes a first digit associated with a percentage of teeth in the individual's dentition in need of treatment and a second digit associated with a percentage of teeth in the individual's dentition previously treated for a carious condition.

8. The method of claim 1, wherein the prosthetic score includes a first digit associated with the magnitude of need to replace teeth in the individual's dentition and a second digit associated with a percentage of prosthetic teeth that comprise a dentition that is optimal for the individual.

9. The method of claim 1, further comprising:
storing the caries score and the prosthetic score;
repeating, at a subsequent time, the classifying the teeth the individual's dentition, calculating the caries score, and calculating the prosthetic score; and
generating a graph of the changes in the individual's caries score and prosthetic score over time.

10. The method of claim 1, wherein calculating the caries score further comprises:
calculating a percentage of teeth in the individual's dentition with caries;
calculating a percentage of teeth in the individual's dentition previously restored from a carious condition;
determining a carious value for carious teeth based on the calculated percentage of teeth in the individual's dentition with caries;
determining a restored value for restored teeth based on the calculated percentage of teeth in the individual's dentition previously restored from a carious condition; and
determining the caries score based on the carious value and the restored value.

11. The method of claim 1, wherein calculating the prosthetic score comprises:
determining a percentage of teeth in the individual's dentition in need of replacement;
determining a value for tooth replacement; and
calculating the prosthetic score based on the determined values.

12. The method of claim 1, wherein the stored look up table comprises a table classifying potential caries scores into at least three classifications related to the health of the individual's dentition, wherein the at least three classifications include:
a first classification including a caries score associated with natural health of the dentition;
a second classification including a first range of caries scores associated with previous carious conditions that have been fully restored; and
a third classification including a second range of caries scores indicating existing disease and need for treatment.

13. The method of claim 1, wherein the stored look up table comprises a table classifying potential prosthetic scores into at least three classifications related to the health of the individual's dentition, wherein the at least three classifications include:
a first classification including a prosthetic score associated with an optimal and natural health of the dentition;
a second classification including a first range of prosthetic scores associated with previous tooth loss conditions that have been fully prosthetically repaired; and
a third classification including a second range of prosthetic scores indicating existing tooth loss that is in need of prosthetic treatment.

14. The method of claim 1, further comprising:
retrieving a stored historical caries score for the individual;
calculating a caries score based on a current status of the individual's dentition, wherein the calculation generates an increased caries score with increased need and decreased caries score with effective treatment; and
comparing the caries score to the historical caries score, and
communicating a change in the status of the individual's dentition based on the comparison of the caries score to the historical caries score where in increased score indicates a worsening condition and a decreased score indicates a decrease in need for treatment.

15. The method of claim 1, further comprising:
retrieving a stored historical prosthetic score for the individual;
calculating a prosthetic score based on a current status of the individual's dentition, wherein the calculation generates an increased prosthetic score with increased need and decreased prosthetic score with effective treatment; and
comparing the prosthetic score to the historical prosthetic score, and
communicating a change in the status of the individual's dentition based on the comparison of the prosthetic score to the historical prosthetic score where in increased score indicates a worsening condition and a decreased score indicates a decrease in need for treatment.

16. The method of claim 1, wherein the computer system configured to calculate a caries score and the prosthetic score comprises a computer system configured to execute machine readable instructions that when executed cause the computer system to calculate the caries score and the prosthetic score.

17. A method for describing a status of an individual's teeth over time, the method comprising:
generating information about the status of the individual's teeth using a computer system configured to calculate a caries score and a prosthetic score based at least in part from a stored look-up table by:
calculating by the computer system, based on at least a number of teeth that are optimal for the individual, a number of teeth in the individual's dentition that are visible, a number of teeth with restoration, and a number of teeth having caries or a defective restoration, the caries score associated with the extent of teeth in the individual's dentition effected by decay; and
calculating by the computer system, based on at least the number of teeth that are optimal for the individual, the number of teeth in the individual's dentition that are visible, a number of teeth that have been replaced and are removable and a number teeth that have been replaced and are not removable, the prosthetic score associated with the status of the individual's dentition related to prosthetic tooth replacement,
wherein the caries score and the prosthetic score each increase with increased need for treatment and decrease with effective treatment.

18. The method of claim 17, wherein:
an increasing caries score is correlated to a worsening condition in which the individual's dentition includes an increased number of teeth in need of treatment;
a decreasing caries score indicates successful treatment of carious lesions in the individual's dentition;
an increasing prosthetic score is correlated to a worsening condition in which the individual's dentition includes an increased number of missing teeth that need to be replaced; and
a decreasing prosthetic score indicate successful replacement of needed missing teeth in the individual's dentition.

19. A method for describing a state of an individual's teeth over time, the method comprising;
generating information about the status of the individual's teeth using a computer system configured to calculate a caries score and a prosthetic score based at least in part from a stored look-up table by:

calculating by the computer system, the caries score associated with the extent of teeth in the individual's dentition affected by decay, the caries score including a first digit associated with a percentage of teeth in the individual's dentition in need of treatment and a second digit associated with a percentage of teeth in the individual's dentition previously treated for a carious condition; and calculating by the computer system, the prosthetic score associated with the status of the individual's dentition related to prosthetic tooth replacement, the prosthetic score including a first digit associated with the magnitude of need to replace teeth in the individual's dentition and a second digit associated with a percentage of prosthetic teeth that comprise a dentition that is optimal for the individual;

storing the caries score and the prosthetic score;

repeating, at a subsequent time, the classifying the teeth the individual's dentition, calculating the caries score, and calculating the prosthetic score; and generating a graph of the changes in the individual's caries score and prosthetic score over time.

20. The method of claim 19, wherein:

the caries score and the prosthetic score each increase with increased need for treatment and decrease with effective treatment and an increasing caries score is correlated to a worsening condition in which the individual's dentition includes an increased number of teeth in need of treatment;

a decreasing caries score indicates successful treatment of carious lesions in the individual's dentition;

an increasing prosthetic score is correlated to a worsening condition in which the individual's dentition includes an increased number of missing teeth that need to be replaced; and a decreasing prosthetic score indicates successful replacement of needed missing teeth in the individual's dentition.

21. The method of claim 19, wherein calculating the caries score further comprises:

calculating a percentage of teeth in the individual's dentition with caries;

calculating a percentage of teeth in the individual's dentition previously restored from a carious condition;

determining a carious value for carious teeth based on the calculated percentage of teeth in the individual's dentition with caries;

determining a restored value for restored teeth based on the calculated percentage of teeth in the individual's dentition previously restored from a carious condition; and determining the caries score based on the carious value and the restored value; and calculating the prosthetic score comprises:

determining a percentage of teeth in the individual's dentition in need of replacement;

determining a value for tooth replacement; and calculating the prosthetic score based on the determined values.

* * * * *

UNITED STATES PATENT AND TRADEMARK OFFICE
CERTIFICATE OF CORRECTION

| | |
|---|---|
| PATENT NO. | : 8,206,154 B2 |
| APPLICATION NO. | : 12/173510 |
| DATED | : June 26, 2012 |
| INVENTOR(S) | : John A. Martin and Carl F. Loeb |

It is certified that error appears in the above-identified patent and that said Letters Patent is hereby corrected as shown below:

Claim 1, Column 14, Line 21 – delete "mad" and insert -- and --, therefor.

Claim 12, Column 15, Line 29 – delete "look up" and insert -- look-up --, therefor.

Claim 13, Column 15, Line 42 – delete "look up" and insert -- look-up --, therefor.

Claim 19, Column 16, Line 63 – delete "comprising;" and insert -- comprising: --, therefor.

Signed and Sealed this
Fourteenth Day of August, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,206,154 B2 | Page 1 of 1 |
| APPLICATION NO. | : 12/173510 | |
| DATED | : June 26, 2012 | |
| INVENTOR(S) | : John A. Martin and Carl F. Loeb | |

It is certified that error appears in the above-identified patent and that said Letters Patent is hereby corrected as shown below:

Title Page 1, Section (57) ABSTRACT, line 5, delete "dentitions" and insert -- dentition --

Column 3, Line 2, delete "in" and insert -- an --

Column 3, Line 16, delete "in" and insert -- an --

Column 3, Line 53, delete "teeth the an" and insert -- teeth in an --

Column 4, Line 46, delete "Score" and insert -- score --

Column 6, Line 23, delete "replaces" and insert -- replaced --

In Claim 9, Column 15, Line 3, delete "the teeth the" and insert -- the teeth in the --

In Claim 14, Column 15, Line 65, delete "in" and insert -- an --

In Claim 15, Column 16, Line 13, delete "in" and insert -- an --

In Claim 19, Column 17, Line 19 (Approx.), delete "the teeth the" and insert -- the teeth in the --

Signed and Sealed this
Nineteenth Day of February, 2013

Teresa Stanek Rea
*Acting Director of the United States Patent and Trademark Office*